United States Patent [19]
Guering et al.

[11] Patent Number: 5,146,282
[45] Date of Patent: Sep. 8, 1992

[54] PROCESS AND DEVICE FOR MEASURING THE OPTICAL QUALITY OF A GLAZING

[75] Inventors: Paul Guering, Paris; Patrick Gayout, Gagny, both of France; Philippe Vizet, Aachen, Fed. Rep. of Germany

[73] Assignee: Saint-Gobain Vitrage International, Courbevoie, France

[21] Appl. No.: 720,696

[22] Filed: Jun. 25, 1991

[30] Foreign Application Priority Data

Jun. 25, 1990 [FR] France ................ 90 07924

[51] Int. Cl.$^5$ ............................................. G01N 21/88
[52] U.S. Cl. ...................................... 356/239; 356/127; 358/106
[58] Field of Search ................ 356/239, 240, 127; 358/106

[56] References Cited

U.S. PATENT DOCUMENTS

| | | | |
|---|---|---|---|
| 4,299,482 | 11/1981 | Task | 356/124 |
| 4,398,822 | 8/1983 | Task | 356/239 |
| 4,453,827 | 6/1984 | Taboada | 356/127 X |
| 4,647,197 | 3/1987 | Kitaya et al. | 356/239 |

FOREIGN PATENT DOCUMENTS 58-52504  3/1983  Japan ................... 356/239

Primary Examiner—Vincent P. McGraw
Attorney, Agent, or Firm—Oblon, Spivak, McClelland, Maier & Neustadt

[57] ABSTRACT

A method for evaluating the optical quality of a glazing using a projection technique in which the shadow of glazing (3) projected with a localized light source (2, 15) is analyzed by a camera (6) assisted by a computer. The illumination at a point (M) of screen (4) is compared to the illumination at same point (M) in the absence of glazing (3) and the measurement is weighted by the optical and geometric parameters of corresponding point (m) of glazing (3). The resolving power in one direction is adjustable by the modification of the dimension of the source in this direction. Application is to the inspection of windshields on a production line.

15 Claims, 4 Drawing Sheets

FIG_2

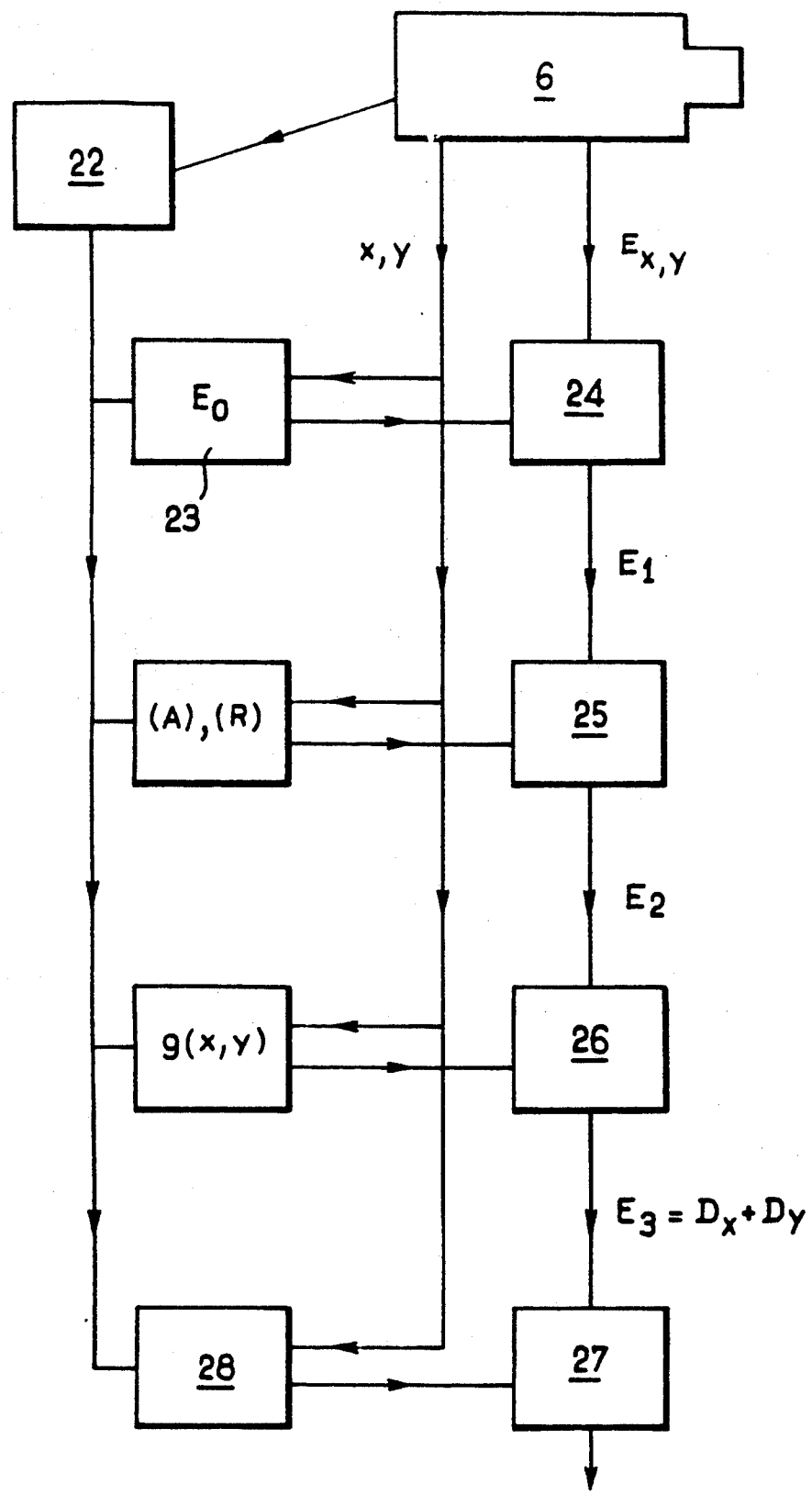
FIG_5

PROCESS AND DEVICE FOR MEASURING THE OPTICAL QUALITY OF A GLAZING

BACKGROUND OF THE INVENTION

1. Field of the Invention

The present invention relates to a technique for measuring optical defects of glazings and particularly motor vehicle glazings.

2. Description of the Related Art

Industry increasingly seeks to control the quality of the products that it produces. This is true in particular of the optical quality of glazings. To achieve this object, all the production parameters are kept in very narrow ranges. Nevertheless, a mishap is always possible, and, even if it is detected, its effect on the product quality is not always known so that an inspection of the quality of 100% of the production is essential in many cases.

For glazings, there is often a need to continuously evaluate their optical quality. It may be desired, in particular, to select the glazing leaving the production lines for a particular use, such as, for example, a mirror intended for scientific applications or a thin flat glass intended to be transformed into a very inclined windshield. In general, moreover, the optical quality of the windshields of modern motor vehicles must be thoroughly controlled. This criterion touches on the safety of the motor vehicles. Further, the shapes of the windshields, their inclination, the materials from which they are produced—very thin glasses or even transparent polymers—require a very elaborate inspection of the optical quality, often for 100% of the product.

The existing inspection methods mainly use projection techniques, either with a localized beam such as, for example, that of a laser, or by projecting a test pattern through a zone of the windshield. A technique using a localized beam, such as that of U.S. Pat. Nos. 4,398,822 or 4,453,827, which relate to aircraft windshields, makes possible a precise measurement, in particular of the angular deviation undergone by the light rays in going through the concerned location, but it requires very long measuring periods if it is desired to have an overall evaluation of the windshields. And this is the case when it is desired to be certain that a defect limit value is not reached by any of the motor vehicle windshields accepted in the output inspection of a production line.

The other known methods are global methods. That of U.S. Pat. No. 4,299,482, which performs a Fourier transform of the image of a striated screen as it is seen through the windshield, requires the making of a photographic printing plate and is thereby unsuited to a continuous inspection during production. The method described in German patent application DE 36 00 199 uses a moire generated between a striated screen and the projection through the windshield of an identical test pattern that is made to rotate slightly relative to the screen to obtain, in the absence of defects, rectilinear moire fringes. The deformation of the fringes is observed by eye and the measurement of the greatest deformation gives information about the greatest optical defect of the concerned field. But the display method would be very difficult to automate.

U.S. Pat. No. 4,647,197, on the other hand, proposes automating a conventional display method. Regular rectilinear scratches carried by a screen are observed through the windshield with a special camera. The scanning that is performed with a given speed makes it possible to "measure" the width of the dark or light lines in the direction of the scanning and to deduce from it data on the corresponding defect. This technique, which is based on a well-known standardized method, cannot provide better results. Moreover, the automation has limits which restrict the possibilities of the display method even more. In the standardized method, a global observation by eye makes it possible to locate the zone of the largest defect quickly, a measurement will then be made at the exact location where the width of the striped lines is at its optimum. The automatic measurement, on the other hand, performs a scanning with a defined span (it is 10 mm in the plane of the windshield in U.S. Pat. No. 4,647,197) and the optical effect is measured only at these specific locations: the risk is therefore great of not detecting the maximum defect. Further, the limits of a method which determines the thickness of striped lines in a single direction are well known; if the greatest defect does not have its dominant effect perpendicular to the lines, its value will be underestimated.

SUMMARY OF THE INVENTION

The present invention proposes providing a method for measuring the focal power of a glazing which detects the greatest defect of the glazing whatever its orientation may be, which evaluates it with a precision greater than ±5 millidiopters, which makes the complete measurement of the glazing in a period at least equal to the production time of the glazing, in particular in the case of windshields, and which makes it possible to follow the evolution of the quality of the glazings produced over time.

It is known to illuminate a transparent object with an approximately pinpoint light source and to observe the projected image on a screen. This technique, known as a "shadowgraphic method," makes it possible to locate the defects of focal power of the object, in particular of a glazing. Where a converging lens is used, the light rays are brought together and more greatly illuminate the concerned zone of the screen, while the concerned zone darkens in the case of a diverging lens.

A method of this type has been described in French patent FR 2 182 254. It is applied there in the observation by reflection of a glass sheet produced as a continuous ribbon. In this type of method, the display evaluation can only be qualitative because the eye is incapable of evaluating the differences of brightness quantitatively. Thus, when these methods are used in the windshield production units, it is necessary to perform a qualitative inspection during production or at the end of the line. This inspection makes it possible to eliminate a random defect which can be created during stages of the production of a laminated windshield. For example, when two flat glass sheets cut out in the dimension of the windshield are assembled on one another to be bent thermally, it can happen that a tiny splinter of glass is found between the two plates, which will consequently deform to get around it. If this defect were not detected at the end of the bending, the space between the two glasses would be filled with the interlayer plastic during the assembly and a very localized converging lens thus would be created. The shadowgraphic method makes it possible to detect such defects during or at the end of the production and to eliminate the concerned windshield.

A method has been proposed to evaluate quantitatively the illuminations of a shadowgraphic image, to deduce from it the values of the optical power. European patent application EP 0 342 127 proposes to observe the shadowgraphic image of a glass ribbon obtained by reflection when it is illuminated under grazing incidence with the diffuse light of a light source with a large surface. The comparison of the measurements made along a straight line perpendicular to the axis of the dominant defects makes it possible—after digital processing of the obtained signal—to measure the defect in a preferred direction.

The device of the present invention uses an assembly of the type used in the shadowgraphic method and makes measurements of illumination of the projected shadow.

The invention has as an object to provide a process for measuring and inspecting the optical quality of a glazing in which it is illuminated with a localized light source and where the shadowgraphic image obtained on a screen is recorded and where the illumination noted at a point (M) is weighted as a function of the illumination which exists at same point (M) in the absence of glazing and as a function of the geometric and optical characteristics of corresponding point (m) on the glazing. The geometric characteristics of point (m) of the glazing comprise the angle of incidence ($\alpha$) on an element of small dimensions and the source-element distance ($L_1$). The optical characteristics are the absorption and the reflection of the glass and the spectral characteristics of the source as viewed by the camera. In the process of the invention, a computer associated with the camera performs the weighing.

The method of the invention is particularly suitable when the glazing is a motor vehicle windshield. The latter is identified with the image of its contour by use of shape recognition software.

In the process of the invention, the elements of the calculation are such that the measured magnitude at any point is the deformation. This value is compared to different limits according to the concerned zone of the windshield, the limits in the various zones being stored in the computer associated with the camera.

The localized light source is limited in size by a diaphragm located at the exit and of the objective of a projector. Further, the object plane at the output of the condenser has its image focused by the objective on the screen. The resolving power of the method in a given direction is equal to the dimension of the beam at the position of the windshield.

The invention also has as an object a device for carrying out the above method. The device may comprise a CCD matrix camera associated with a computer. The latter stores the image obtained on the screen in the absence of glazing and evaluates the optical characteristics at point (m) of the glazing from angle of incidence ($\alpha$) on the corresponding element, and absorption values (A) and reflection values (R) under normal incidence.

The invention also relates to the inspection of motor vehicle windshields on a production line.

The technique of the invention thus makes it possible to measure separately the viewing zone of a windshield and its peripheral zone, in periods less than the production time of the windshield. This technique also makes it possible to make the measurement either under the conditions of vision of the driver or under the conditions of standard tests. Following production, the method makes it possible to detect the degradation of the optical quality over the production run.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 is a complete diagram of the operations of the calculation to be performed.

DETAILED DESCRIPTION OF THE PREFERRED EMBODIMENT

The invention uses the usual shadowgraphic technique which consists in illuminating a glazing with a projector and in observing the shadow on a screen.

Figure 1:
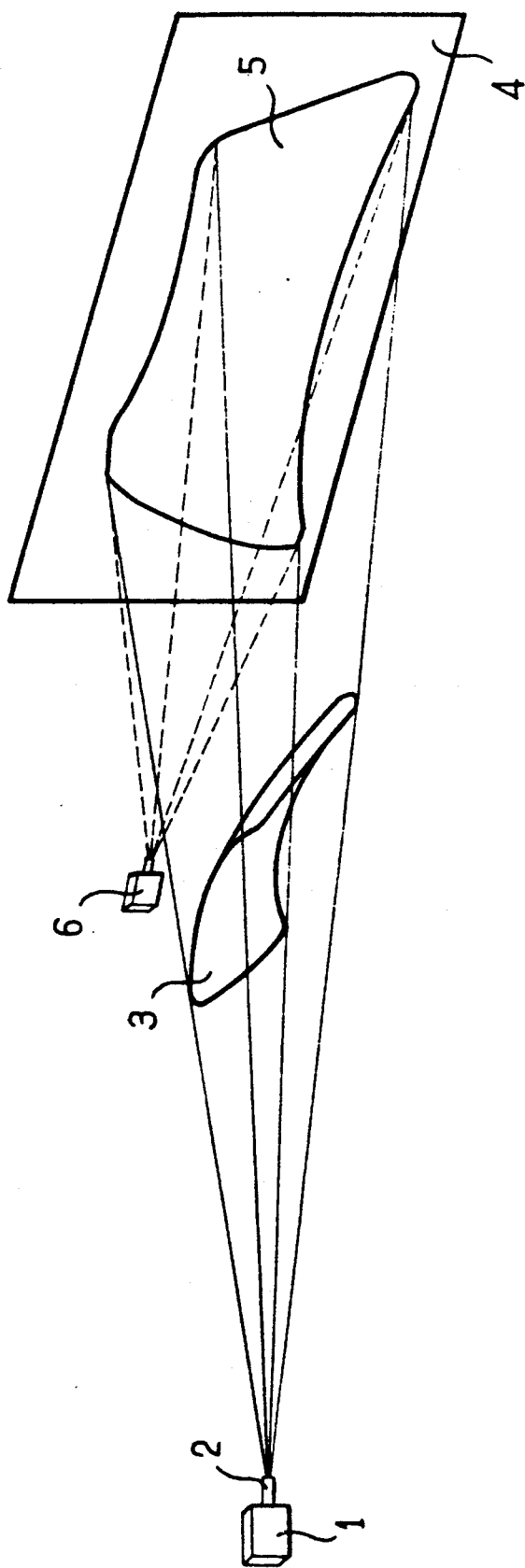
FIG. 1 diagrammatically shows the principle of the method of the invention.

In FIG. 1, the projector having a diaphragm provides a pinpoint source 2. The light coming from 2 illuminates the glazing (a windshield) 3 placed at a great distance (for example, 4 meters) from light source 2. Glazing 3 is placed under the conditions in which it is desired to detect the effect produced by the optical power defect. It is known that for a given geometric structure of the defect of the glass, the optical effect of the structural defect depends greatly on conditions of observation such as relative distances of the observer, the glazing and the object, and the angle of incidence.

In the case of windshields, to have an idea of the visual comfort of the driver, it is necessary to make the observation under the actual conditions. This is why in the device for shadowgraphic observation, the windshield is generally inclined as on the vehicle and the optical axis of the projector is horizontal and parallel to the axis of the vehicle.

A vertical screen 4, on which shadowgraphic image 5 of windshield 3 is projected, is positioned in front of the windshield at a distance which is, for example, 4 meters.

Still in FIG. 1, a video camera 6 is positioned such that it can observe the whole shadow of the windshield on the screen. It may be a CCD matrix camera, for example, model 4712 of COHU, Inc. (San Diego, Calif, USA). The latter, which can work at low illumination of 0.2 lux, has 699 horizontal lines by 580 vertical lines. Under usual conditions, a surface of 2×2 mm on the screen forms one measuring point on the camera detector.

The location of the camera is not decisive in itself, so long as it can obtain an undeformed view of the entire windshield. The camera will advantageously be placed, for example, just above the windshield and on the vertical line of the optical axis of the projector as seen in FIG. 1.

Figure 2:
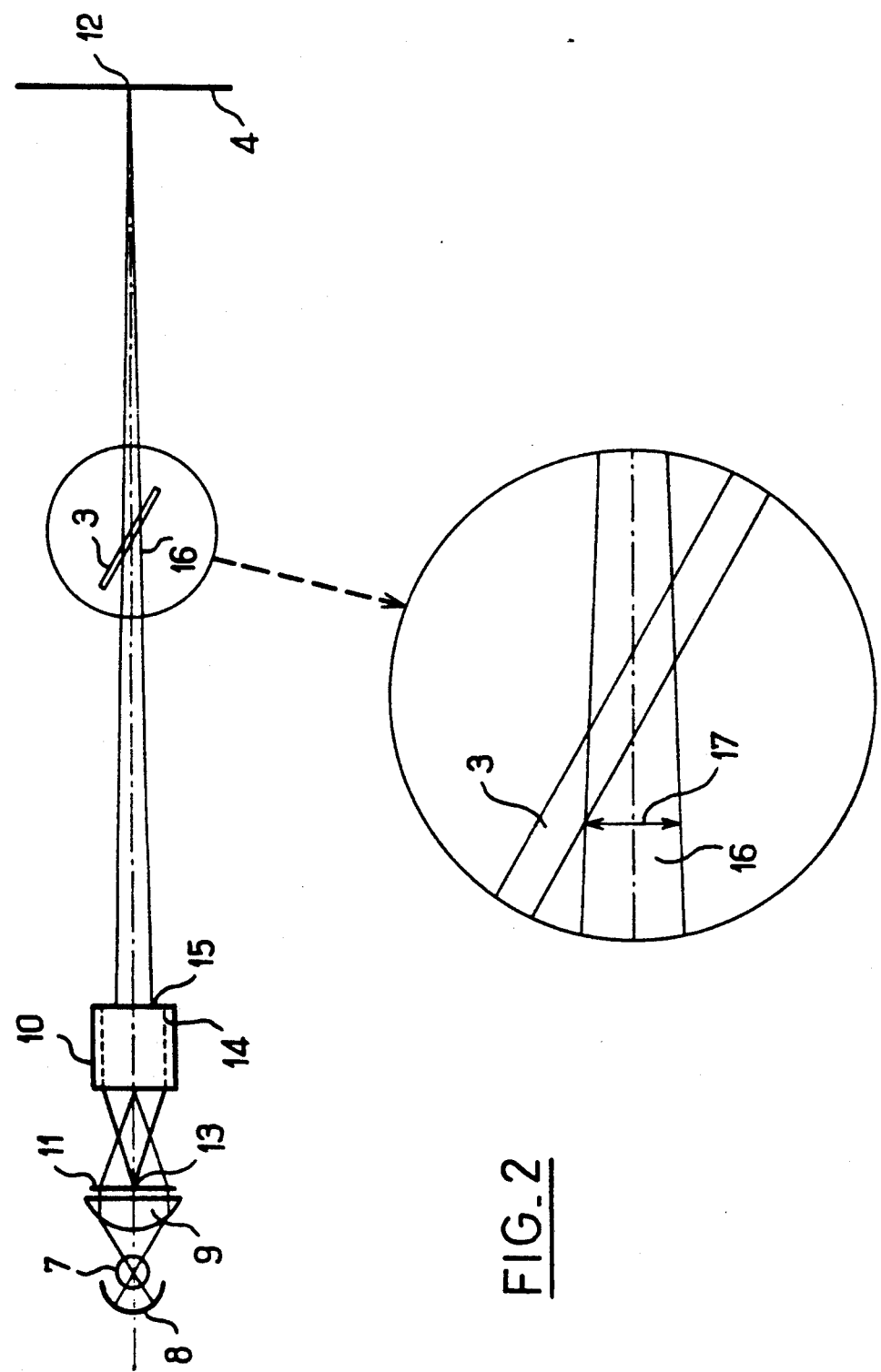
FIG. 2 illustrates the resolving power of the method of the invention.

FIG. 2 is a diagrammatic view of projector 1. The tungsten filament lamp is seen at 7, it is made of silica with a halogen atmosphere and is at the focal point of a spherical mirror 8. Condenser 9 focuses an image of the filament at the input of objective 10. The usual location of the slide is shown at object plane 11. The objective is adjusted to project onto screen 4 the image of the slide at object plane 11; i.e., a sharp image of point 13 on the axis of the slide is obtained at point 12. The beam emitted by the projector 1 at the output of its objective 10 is limited by a diaphragm. Its original diameter represented at 14 is reduced at 15 by the diaphragm (not shown). The light spot at 15 should meet two conditions, one relates to illumination and the other relates to its shape and dimensions. The projector should first of all guarantee a perfectly homogeneous illumination of the beam at 15. Further, the diaphragm should have such dimensions that at the level of the glass, the light beam which forms the image has, in a given direction, a width which is equal to the resolving power that it is desired to give in this direction.

In FIG. 2, the beam 16 at the position of glazing 3 has a vertical dimension d shown at 17 when first going through the glass. Magnitude d is the resolving power in the vertical direction.

Figure 3:
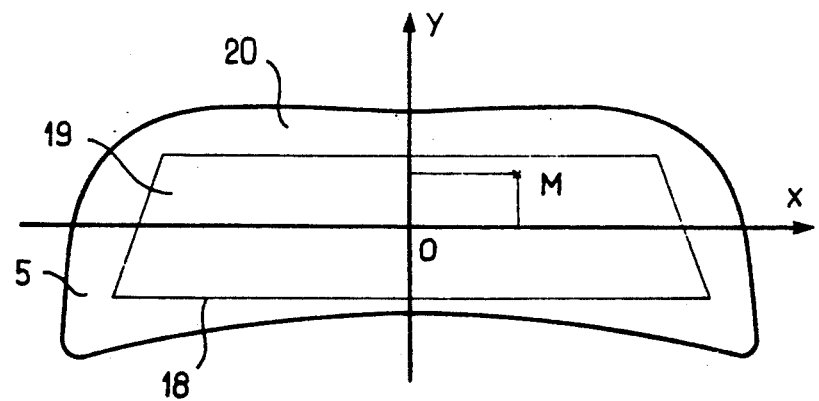
FIG. 3 shows the different zones of the windshields.

Shadow 5 of windshield 3 on screen 4 has been shown in FIG. 3. A frame which delimits two zones in the windshield, a main vision zone 19 and a peripheral zone 20, is seen at 18.

This separation into zones results from a standard (R 43 of the ECE, for example) or specifications of the manufacturer. The limits of the values of the optical defects for each zone are not the same. During a measurement, frame 18 between the two zones is not visible on the screen: it is instead stored in the memory of a computer associated with video camera 6. Likewise, the measurement limit at the periphery of the windshield is also stored in memory.

Each type of windshield which is to be observed by camera 6 is identified during its passage either by data transmitted manually by the operator or by the shape of contour 5 on the screen being "recognized" by the camera-computer unit before any new measurement. It is possible that this recognition can occur even if the camera has never "seen" the projected shadow 5 before. The criteria provided by a motor vehicle manufacturer to a windshield supplier are carried out most often in the context of computer-aided design (CAD) on a data-processing storage medium. From the provided data which generally comprises data making it possible to delimit two zones 19 and 20, the computer is made to calculate the position that the circumference of the shadowgraphic image of the windshield will have on the screen and that which frame 18 would have if it were applied on windshield 3. As a result, the subsequent identification of the type of windshield which is in the test booth and the positioning of a point of the shadowgraphic image relative to zones 19 and 20 are made possible.

In FIG. 3, there is also shown a system of axes (ox, oy) by which the camera and computer associate a pair of coordinates (x, y) with each point M of the shadowgraphic image. That is, any point on the screen 4 is assigned an x,y coordinate by the computer. This coordinate data is important because it makes it possible, when a defect has been detected at point M, to locate the defect relative to zones 19 and 20, to compare it to the limit values established for each of zones 19 and 20 (to which the various x, y coordinates are assigned), and optionally to initiate an exact marking or to study carefully the origin of a systemic defect.

The principle of the digitization of the shadowgraphic image consists in performing the following calculation:

$$E_3 = D_x + D_y = g(x,y)\left[\frac{E}{E_{x,y}} - 1\right]P_m$$

Dx is the deformation of the glazing at the point m in direction Ox which produces an aberration of the optical power in this same direction; $D_y$ is the corresponding deformation in direction Oy.

$E_{x,y}$ is the illumination of the screen at point M with coordinates x and y, without any glass.

E is the illumination that would exist at M if the glass were without optical defects but taking into account the phenomena of light attenuation due to reflection and local light transmission.

g (x,y) is a geometric term.

$P_m$ is a length corresponding to the span of a test pattern projected on the screen in the manual evaluation method (which is to be complied with).

Figure 4:
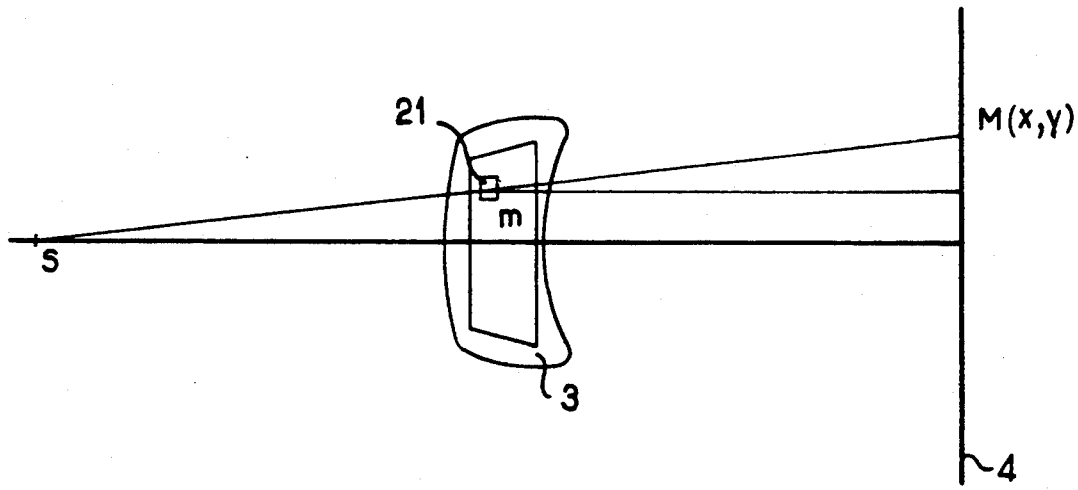
FIG. 4 shows one of the corrections to be applied in the calculation of the optical power.

In FIG. 4, it is seen that according to the location in the windshield of point m, whose projection is point M(x,y), the geometric conditions such as the distance Sm between the source and the windshield, or the windshield-screen distance, are different. The term g (x,y) takes into account this magnification, which is different for each element 21 of the windshield. Since this term varies very little, it is not necessary to clutter the memory of the computer with values for each point, a calculation for each small element 21 of, for example, 10×10 cm, is sufficient in the case of a windshield of simple shape. The expression which makes it possible to calculate g (x,y) is:

$$g(x,y) = \frac{L}{L_1 + \sqrt{x^2 + y^2} \cdot \tan\alpha}$$

where L is the source-screen distance, $L_1$ the distance between source 2 and element 21, and $\alpha$ is the angle of inclination of element 21 in which is found the point m in question, i.e., the angle between the plane of element 21 and a plane perpendicular to the axis of the projector.

In FIG. 5, there is shown a block diagram of successive operations to be performed by the computer which is associated with camera 6.

Before beginning a series of measurements, it is necessary to supply the memory of the computer with all the data needed to perform the work.

In FIG. 5, this memory is symbolized by box 22. Here, all the data on the windshield itself is stored: the contour of its shadow projected on the screen, which will make it possible by using shape-recognition software and data from the camera, to identify the windshield and to access the files where the data is stored which is useful for the necessary calculations, such as the range of values of x an y which correspond to each of zones 19 or 20 or the values of the specific parameters for each small element 21. The latter comprise its angle $\alpha$, the actual value of the light transmissivity T of the glazing, its light reflectivity R, distance $L_1$ between light source 2 and element 21 and distance $L_2$ between point m and screen 4.

The upper limits tolerated for the defect $D_x+D_y$ respectively in zone 19 and in zone 20 are also stored in memory 22.

The sequence of the operations of the measurement of the focal power of a windshield is as follows: before the arrival of the windshield, camera 6 records the illumination $E_o$ of each point M (x,y) of its field of vision. Actually, the illumination given by a projector such as 1 is not the same in each point and the stored illumination values $E_o$(x,y) will serve as a reference for the sequence of operations. This data is stored in memory 23. Upon the arrival of the windshield in the field, the picture of the shadowgraphic image is taken. The latter is made at 1/25th of a second and so the windshield need not be immobile. It can move 5 mm or even 10 mm. The first operation is its identification, either automatically by shape recognition as discussed above, or by manual input by an operator. The two techniques can be used at the same time; the identification of the windshield by its shape may be performed automatically and the nature (thickness, color) of the glazing may be introduced by the operator, for example.

The first measuring operation is performed in block 24. It consists in modifying illumination value $E_M$ measured by the camera at point M having coordinates x and y with value $E_o$ measured at the same point in the absence of a windshield, to produce value $E_1$.

$$E_1 = \frac{E_M - E_0}{E_0}$$

The second operation which is performed in block 25 consists in correcting value $E_1$ for all the variations of light intensity which have an origin other than the optical power defect that is to be measured. These are—apart from the smears which are random—the light variations due to absorption and reflection. They have been predetermined under normal incidence and are stored as curves A ($\lambda$) and R ($\lambda$) (not shown) which characterize the spectral absorption and reflection of the glass, and S ($\lambda$) which is the spectral characteristic of the light source as well as C ($\lambda$) which is that of the camera. These elements (A and R under normal incidence) undergo variations as a function of angle $\alpha$. For each element 21, the following calculation will therefore be performed:

$$E_2 = \frac{E_1}{1 - A(\alpha) - R(\alpha)}$$

In block 26, the correction of distance g (x,y), already mentioned, is calculated:

$$E_3 = g\ (x,y) \cdot E_2 \cdot P_m$$

This value $E_3 = D_x + D_y$ is the resultant of magnifications at x and at y caused by the focal power defect located at point M of the windshield.

The last operation consists in comparing this value $E_3$ to the limits that have been established for production. It is performed in block 27 from limits stored in memory element 28 as a function of zone 19 or 20. The final operation ends with the display of the result. It can be performed in various manners, one of which consists in making the results appear in a video image representing the windshield with frame 18 superimposed thereon. In each of the two zones 19 and 20, each point of the image has a different color depending on whether the focal power at this point is less than or greater than its corresponding limit.

The above process is repeated for each point m as the camera scans the windshield.

Another way to use the results on a production line consists in providing a response of the "stop or go" type: the good windshield, which in each of its two zones 19 and 20 has a focal power less than the corresponding limit, follows one circuit at the output of the inspection booth. The other follows a deviated circuit and receives at the output of the booth a self-adhesive tag on which a printer has recorded the value and the location of the defect causing the rejection.

One of the advantages of the method and of the device which have just been described resides in the possibility of fitting their resolving power to the standards or to the existing inspection processes.

The existing methods which evaluate the shadowgraphic image of a known glazing such as, for example, that described in European patent application EP 0 342 127, use systems for scanning in one direction at a given speed and analyze the signal by performing a frequency filtering to eliminate the defects whose width is less than a certain value.

The methods which are standardized or used in the motor vehicle industry use techniques for projecting test patterns consisting of striped lines through the windshield and have resolving powers—for the component of the defect perpendicular to the lines—which is the thickness of the line at the level of the windshield.

When the method of the invention is used to obtain the most complete data on the optical quality of the windshield, a diaphragm at 15 (FIG. 2) which provides a beam 16 with circular section at the level of the windshield is used. Its diameter 17 is chosen to be equal to the minimum width of the defect to be detected. Any defect of smaller width will not involve in an appreciable way the illumination of the screen.

In the case where it is desired to obtain measuring results in accordance with those obtained under the standardized conditions of a process using a particular striped test pattern, it is possible to project beam 16 through the plane of the glass, in a direction perpendicular to that of the stripes of the test pattern, with the same dimension 17 as that, at this level, of the lines of the standard projected under the same conditions. If another dimension is greater or if the section is circular but the defects of the windshield have a preferred direction and act only perpendicular to the lines of the test pattern, then the defect detected is that which the manual standardized methods would have detected.

The second case mentioned above: preferred direction of action of the defects perpendicular to the lines of the test pattern is the rule for the inspection-reception systems of the motor vehicle industry when systemic defects—such as those due to the shape of the windshield—exist; the manual inspection method seeks to measure the latter. Therefore, the process of the invention will detect them automatically. In the case where the defects have a random direction, however, the method of the invention is more exact than the manual methods: it will never allow a defect to pass which would have been stopped by the latter. This last remark applies also for possible traces of sears, which would have appeared on the windshield during phases of its production. It is not ruled out that such a defect is interpreted by the method of the invention as a negative optical power defect (diverging lens). But, on the one hand, this extremely rare error would be immediately detected by the systematic visual examination which follows the rejection of the windshield and in any case, the inspection of the method of the invention can only be safer than the existing inspections.

The device and the method proposed by the invention thus make possible a 100% automatic inspection of the entire production of a windshield production line. They make it possible to establish different limits for different zones in each type of windshield. They measure the optical power defect whatever its direction of action may be. They have the resolving power that is desired. Finally, they select an optical quality with criteria at least as exact as that of the methods used in the motor vehicle production lines.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for measuring and inspecting the optical quality of a glazing, comprising the steps of:
   illuminating a point on a glazing with light from a localized light source which passes through said glazing so that an illumination value $E_M$ according to the shadowgraphic image of the point is obtained at a point on a screen;
   recording the value $E_M$; and
   illuminating said point on the screen with a light beam from said localized light source which does not pass through said glazing to produce an illumination value $E_o$;
   calculating a deformation value of the glazing at said point on said screen as a function of the recorded value $E_M$, as a function of the value $E_o$, and as a function of the geometric position of said image on said screen.

2. The process of claim 1 including the steps of comparing said calculated deformation value with a stored value of a maximum acceptable deformation at said point and characterizing said glazing as defective when said calculated deformation value exceeds said maximum acceptable deformation value.

3. The process of claim 2 including the step of illuminating said glazing with said light source so that every point on said glazing is illuminated by said light source and is recorded.

4. The process of claim 1 wherein said calculating step includes storing an angle of incidence of the light from the light source on a portion of the glazing including said point and using said angle as said function of the geometric position.

5. The process of claim 1 wherein said calculating step includes calculating the deformation value of said glazing at said point on said screen as a further function of light absorption and reflection characteristics of said glazing.

6. The process of claim 3 wherein said glazing is a motor vehicle windshield.

7. The process of claim 6 including the steps of storing data corresponding to images of at least two kinds of windshields and identifying the windshield being illuminated by said light source by comparing the recorded images thereof with the stored data.

8. The process of claim 3 wherein said maximum acceptable deformation varies for different ones of said points.

9. The process of claim 1 including the step of selecting the resolving power of the light source in any direction by adjusting the dimension of the light beam from the light source in that direction.

10. A device for measuring and inspecting the optical quality of a glazing, comprising:
    a localized light source for projecting light through a point of a glazing;
    a screen on which the projected light forms a shadowgraphic image of said point;
    a camera for recording said image; and
    a computer including means for calculating a deformation value of the glazing at said point on said screen as a function of the recorded image, as a function of the intensity of the light from said light source on said screen in the absence of said glazing, and as a function of the geometric position of said image on said screen.

11. The device of claim 10 wherein said computer includes means for storing a value of a maximum acceptable deformation at said point, comparing said calculated value with said stored value and characterizing said glazing as defective when said calculated value exceeds said maximum acceptable deformation value.

12. The device of claim 10 wherein said light source includes a diaphragm.

13. The device of claim 10 wherein said camera comprises a CCD matrix camera.

14. The device of claim 10 wherein said calculating means includes means for storing an angle of incidence of the light from the light source on a portion of the glazing including said point and using said angle as said geometric position.

15. The device of claim 10 wherein said calculating means includes means for calculating the deformation value of said glazing at said point on said screen as a further function of light absorption and reflection characteristics of said glazing.

* * * * *